United States Patent [19]

Wong et al.

[11] Patent Number: 4,824,675

[45] Date of Patent: Apr. 25, 1989

[54] DISPENSER WITH MOVABLE MATRIX COMPRISING A PLURALITY OF TINY PILLS

[75] Inventors: Patrick S. L. Wong, Hayward; Felix Theeuwes, Los Altos; Richard Cortese, Los Gatos; James B. Eckenhoff, Los Altos, all of Calif.

[73] Assignee: ALZA Corporation, Palo Alto, Calif.

[21] Appl. No.: 72,506

[22] Filed: Jul. 13, 1987

[51] Int. Cl.⁴ .......................... A61K 9/22; A61K 9/26
[52] U.S. Cl. ................................. 424/438; 424/458;
424/468; 604/892.1
[58] Field of Search ............... 424/438, 464, 466, 469,
424/473, 468, 458; 604/892.1

[56] References Cited

U.S. PATENT DOCUMENTS

| | | | |
|---|---|---|---|
| 3,946,734 | 3/1976 | Dedrick et al. | 604/892.1 |
| 3,995,632 | 12/1976 | Nakano et al. | 128/260 |
| 4,251,506 | 2/1981 | Laby | 424/19 |
| 4,327,725 | 5/1982 | Cortese et al. | 128/260 |
| 4,350,271 | 9/1982 | Eckenhoff | 222/386.5 |
| 4,595,583 | 6/1986 | Eckenhoff et al. | 424/15 |
| 4,612,008 | 9/1986 | Wong et al. | 604/892 |
| 4,659,558 | 4/1987 | Urguhart et al. | 424/486 |
| 4,675,174 | 6/1987 | Eckenhoff | 424/438 X |
| 4,717,566 | 1/1988 | Eckenhoff et al. | 424/438 |
| 4,717,718 | 1/1988 | Eckenhoff et al. | 424/438 X |
| 4,764,380 | 8/1988 | Urquhart et al. | 424/468 X |
| 4,772,474 | 9/1988 | Eckenhoff et al. | 424/438 X |

Primary Examiner—Nancy A. B. Swisher
Attorney, Agent, or Firm—Paul L. Sabatine; Edward L. Mandell; Steven F. Stone

[57] ABSTRACT

A dispenser is disclosed for delivering tiny pills to an environment of use. The dispenser comprising a wall that surrounds an internal space comprising a first mean in the dispenser for changing from a dispenser state to an environment of use state on leaving the dispenser, tiny pills in the first means, and a second means in the dispenser for aiding in displacing the first means for the dispenser.

10 Claims, 2 Drawing Sheets

DISPENSER WITH MOVABLE MATRIX COMPRISING A PLURALITY OF TINY PILLS

This application is copending with applications identified as U.S. patent application Ser. No. 07/054,714 filed May 24, 1987 and U.S. patent application Ser. No. 07/069,148 filed on July 2, 1987.

FIELD OF THE INVENTION

This invention pertains to both a novel and useful dispenser. More particularly, the invention relates to a dispenser comprising a wall that surrounds a lumen. The lumen contains a movable matrix containing a plurality of tiny pills, which tiny pills contain a beneficial agent. The lumen contains also a driving member for pushing the matrix from the dispenser. The dispenser comprises a mouth in the wall having a cross-sectional area substantially equal to that of the lumen for delivering the matrix containing the tiny pills to an environment of use.

BACKGROUND OF THE INVENTION

Dispensers for delivering a beneficial agent to an environment of use are known to the prior art. For example, one dispenser is disclosed in U.S. Pat. No. 3,995,632 issued to patentees Nakano, Higuchi and Hussain. This patent discloses a dispenser comprising a saturated solution of magnesium sulfate that pushes against a melting composition. The melting composition is squeezed through a small passageway from the dispenser. In U.S. Pat. No. 4,251,506 issued to patentee Laby, a device is disclosed consisting of a controlled release composition for administering a therapeutic agent to a ruminant. The patentee discloses in detail a spring for pushing a composition from the dispenser. The use of a spring as a driving force limits the practical use of the device, as the driving force of a spring diminishes by the distance through which the spring operates. For this device, drug delivery decreases over time as the spring elongates and, concurrently, weakens. The delivery rate is influenced also by the nature of the composition and its interaction with fluid as the interfaced environment of use. The interfaced provides exterior mechanical action that controls drug released by the environment and not by the device.

Another dispenser is disclosed in U.S. Pat. No. 4,327,725 by the inventors Cortese and Theeuwes. The dispenser disclosed in this patent comprises a hydrogel that urges an aqueous formulation through a passageway from the dispenser. In U.S. Pat. No. 4,350,271 issued to Eckenhoff, a dispenser is disclosed comprising a water swellable composition that pushes a lipophilic fluid from the dispenser. U.S. Pat. No. 4,612,008 issued to Wong, Barclay, Deters and Theeuwes discloses a dispenser wherein an expanding polymer pushes a drug formulation comprising an aqueous osmotically active solution from the dispenser. Another dispenser is disclosed by patentees Eckenhoff, Cortese and Landrau in U.S. Pat. No. 4,595,583. The dispenser disclosed in this patent comprises an expandable, aqueous activated osmopolymer that urges a heat responsive composition through an orifice of predetermined limited dimensions from the dispenser.

The release of uncoated pellets of drug and coated pellets of drug is disclosed by patentee Blythe in U.S. Pat. No. 2,738,303. In this patent the delivery system disclosed consists essentially of a capsule containing uncoated pellets and coated pellets of drug having varying thickness. On release of the pellets from the capsule the uncoated pellets provide an initial amount of drug and the coated pellets provide drug over a period of time. Another delivery system is disclosed by patentee Sheth et al in U.S. Pat. Nos. 4,140,775 and 4,167,558. The systems disclosed in these patents consist essentially of a tablet formed of a compressed polymer containing dispersed drug. The system is hydrodynamically balanced for remaining in the stomach for releasing drug over time.

The delivery systems of the prior art presented above represent an outstanding and pioneering advancement in the dispensing art and they are, additionally, useful for dispensing innumerable beneficial agents to an environment of use. Now, this present invention has discovered unexpectedly that a dispenser can be made available comprising a novel and an unobvious dispensing means unknown heretofore for delivering a beneficial agent to an environment of use. That is, it now has been discovered that a dispenser can be provided comprising means for delivering a bio-affecting beneficial agent at a kinetically controlled rate substantially equal to its kinetic rate of release from the dispenser. The dispenser thereby makes available to a beneficial agent receptor controlled and constant prolonged delivery of a beneficial agent according to a preselected built-in optimal program of beneficial agent presentation.

OBJECTS OF THE INVENTION

In view of the above presentation it is a principle object of this invention to provide a dispenser comprising novel means for the controlled delivery of a beneficial agent at a rate substantially equivalent to its dispenser-controlled rate of release from the dispenser over time.

Another object of the invention is to provide a dispenser that is simple in construction and which dispenser exhibits all of the practical benefits of controlled and continuous administration of a drug to animals and to humans over a prolonged period of time.

Another object of the invention is to provide a dispenser comprising a reservoir comprising a plurality of tiny pills which reservoir erodes at a controlled rate in a fluid environment of use as it is dispensed from the dispenser and concurrently with the erosion releases tiny pills to the environment of use.

Another object of the present invention is to provide a dispenser that delivers a plurality of tiny pills containing a beneficial agent, which tiny pills are delivered at a controlled rate in a fluid environment of use as a tiny-timed-pill carrier is rate displaced from the dispenser.

Another object of the present invention is to provide a dispenser comprising a pharmaceutically acceptable carrier selected from the group consisting of solid and semi-solid carriers containing tiny pills that are released from the carrier into a fluid environment of use as the carrier is rate displaced from the dispenser.

Another object of the present invention is to provide a dispenser that is self-contained, self-starting and self-powered in a fluid environment of use.

Another object of the present invention is to provide a dispenser comprising a matrix containing tiny pills, which matrix on its release from the dispenser disintegrates and releases the tiny pills.

A further object of the invention is to provide a dispenser comprising a reservoir composition that houses a multiplicity of tiny pills, which tiny pills comprise a drug that is from poorly soluble to very soluble in an aqueous media, which drug now can be delivered at a rate controlled by the dispenser, at a continuous rate for a particular time period, the use of which dispenser requires intervention only for initiation of the drug delivery regimen.

Another object of the invention is to provide a dispenser comprising a reservoir and a plurality of tiny pills, which two members function as a cooperative unit for administering from low to high doses of a drug to the gastrointestinal tract at a controlled rate over a prolonged period of time.

Another object of the present invention is to provide a dispenser comprising an internal lumen containing a carrier comprising a continuous linear body member symmetrical with the axis of the lumen, which carrier contains a plurality of tiny pills with the carrier displaced at a continuous, uninterrupted rate from the lumen over time.

Another object of the present invention is to provide a dispenser comprising an internal capsule arrangement that makes it easier to manufacture the dispenser at a reduced cost thereby extending the usefulness of the dispenser for treating humans and domestic animals.

Another object of the present invention is to provide a dispenser comprising a wall that surrounds a lumen with a mouth in the wall having an opening substantially equal to the cross-sectional area of the lumen, which lumen houses a continuous body member having a plurality of tiny pills dispersed therein and is urged through the mouth for delivering the tiny pills comprising a beneficial agent to an environment of use.

Another object of the present invention is to provide a dispenser comprising a capsule lumen containing a body member comprising a plurality of tiny pills, which body member extends the length of the lumen except for the area occupied by an expandable driving member for urging the body member from the lumen, a semipermeable wall that surrounds the capsule, and an opening having substantially the same dimensions as the lumen for dispensing the body member from the dispenser.

Another object of the invention is to provide a dispenser comprising a semipermeable wall that surrounds, in at least a part, an internal lumen which lumen contains a carrier comprising tiny pills and initially occupies a major portion of the lumen, except for a driving member and an optional densifier, with the dispenser delivering a beneficial agent contained in the tiny pills by the combined physical-chemical operations of the driving member urging the displaceable carrier through an opening in the wall of the environment of use.

A further object of the invention is to provide a dispenser comprising a dense member for keeping the dispenser in the rumen over time, wherein the dispenser administers a complete pharmaceutical dosage regimen for a prolonged period of time, the use of which dispenser requires intervention only for initiation of the regimen.

Another object of the invention is to provide a delivery system manufactured as a dispenser comprising a carrier for a plurality of tiny pills, wherein the carrier keeps its physical and chemical integrity during its stay in the dispenser and changes its physical and/or chemical integrity on its displacement from the dispenser into a fluid environment of use.

Another object of the present invention is to provide a drug delivery system that can deliver a beneficial drug housed in a tiny pill contained in a pharmaceutical carrier that maintains its structure within the delivery system and changes its structure on its delivery into the gastrointestinal tract wherein the pharmaceutical carrier dispenses the tiny pill.

Another object of the present invention is to provide a drug delivery system comprising a pharmaceutical carrier that is a dispensable composition for tiny pills, that is innocuous and which carrier on its displacement from the delivery system releases the tiny pills thereby substantially avoiding mammalian tissue irritation and interaction with mammalian protein tissue.

Another object of the present invention is to provide a delivery system comprising an inner capsule, which capsule houses at least one of a hydrophilic or a hydrophobic pharmaceutically acceptable carrier comprising tiny pills that contain an insoluble to soluble drug, and which carrier, when the delivery system is in operation, is pushed substantially intact and substantially unchanged from the delivery system and changes its physical form on displacement from the delivery system for releasing the tiny pills in the environment of use.

A further object of the invention is to provide a drug delivery device for dispensing a drug to a ruminant, which delivery system comprises an inner lumen containing a nonmeltable and nonaqueous thermoplastic composition, a space occupying member, and a density member, and which thermoplastic composition comprises tiny pills comprising an insoluble to soluble beneficial agent that can be dispensed by the thermoplastic composition after said thermoplastic composition exits the delivery system.

Other objects, features and advantages of the invention will be more apparent to those skilled in the dispensing art from the following detailed description of the specification, taken in conjunction with the drawing figures and the accompanying claims.

BRIEF DESCRIPTION OF THE DRAWINGS

In the drawing figures, which are not drawn to scale but are set forth to illustrate various embodiments of the invention, the drawing figures are as follows:

FIG. 3 is an opened view of the dispenser of FIG. 1 taken in conjunction with FIG. 2, wherein

FIG. 4 is considered with FIG. 3, which

Figure 1:
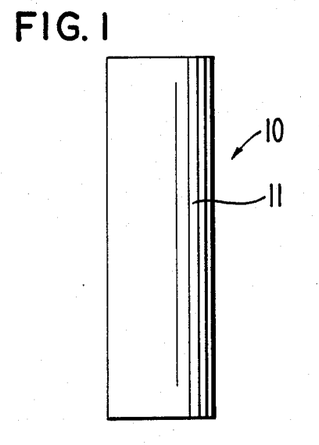
FIG. 1 is a view of a dispenser designed and manufactured for administering a beneficial agent to a warm-blooded animal.
Figure 2:
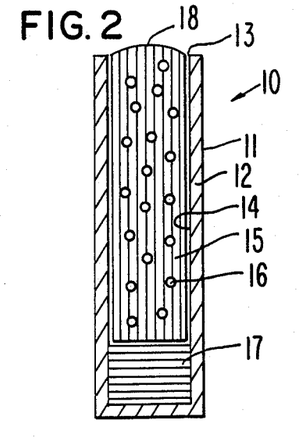
FIG. 2 is an opened view of the dispenser of FIG. 1 through the vertical length of the dispenser for illustrating the structure of the dispenser, wherein the dispenser comprises an internal lumen housing a pharmaceutically acceptable carrier that does not melt at the temperature of an animal's body, and which carrier comprises a continuous body member extending through a major length of the lumen with a plurality of tiny pills dispersed therein, and which lumen contains a space occupying member for pushing the continuous carrier from the lumen.
Figure 3:
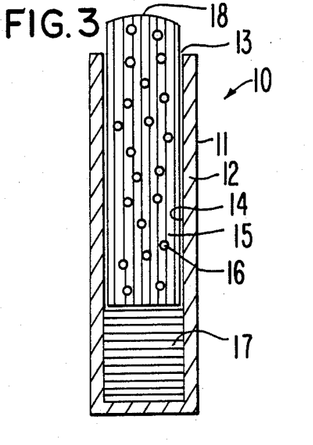
FIG. 3 depicts the dispenser in operation with the carrier formed of a composition that is thermally stable at the temperature of an animal's environment of use, said carrier being urged from the lumen as the space occupying member consumes space in the lumen and, concomitantly, urges the continuous carrier from the lumen of the dispenser for releasing tiny pills in the environment of use.
Figure 4:
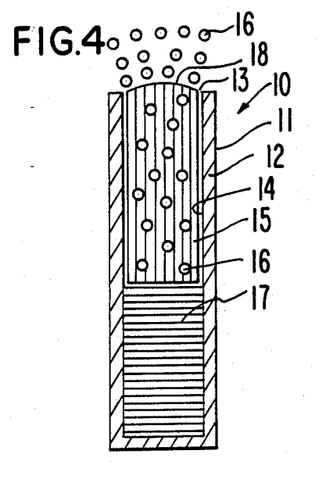
FIG. 4 is seen in opened view depicting a semipermeable wall that surrounds a lumen with the dispenser in operation, wherein the thermally stable carrier severs as it leaves the lumen, enters the environment of use and releases tiny pills, with the main body portion of the carrier still hous means 15 in contact with densifier 19. Densifier 19 is in contact with volume consuming means 17. In this embodiment space consuming means 17 is positioned distant from mouth 13. The presence of densifier 19 in dispenser 10 adapts dispenser 10 for use in a rumen. A rumen retentive dispenser 10 can be manufactured in a variety of sizes and shapes for releasing tiny pills 16 to a ruminant animal. One presently preferred shape is an elongated or lengthened space such as a cylinder shape, or a capsule shape, with a wide mouth. For example, for use with sheep dispenser 10 can embrace an elongated shape and have a diameter of 0.5 inches to 1 inch (1.3 cm to 2.5 cm), and a length of 0.5 inches to 4 inches (1.3 cm to 10 cm). For use with cattle dispenser 10 comprises a diameter of 0.5 inches to 1.5 inches (1.3 cm to 3.8 cm) and a length of about 1 inch to 6 inches (2.5 cm to 15 cm).
Figure 5:
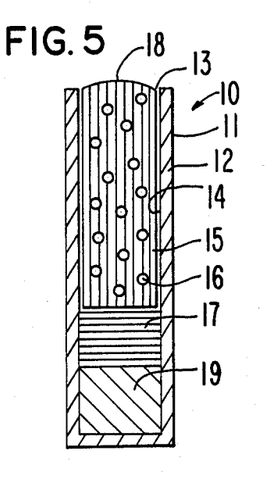
Figure 6:
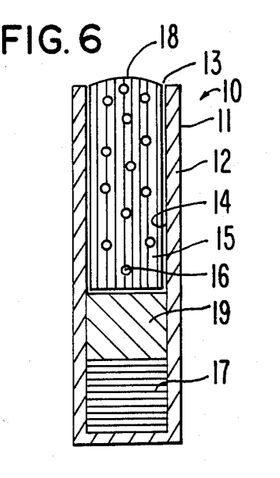
Figure 7:
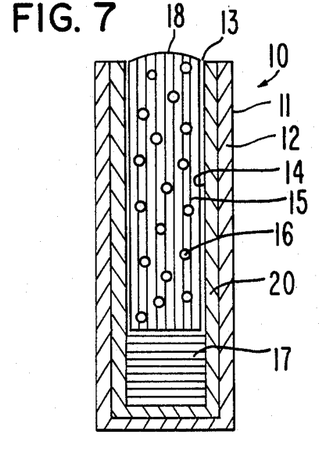

FIG. 7 is an opened view of another embodiment of dispenser 10 provided by the invention. In FIG. 7 dispenser 10 comprises wall 12 that surrounds an internal wide mouth capsule 20. In one presently preferred embodiment comprising internal wide mouth capsule 20, capsule 20 surrounds lumen 14. Lumen 14 contains a nonthermo-responsive carrier 15 containing tiny pills 16. Lumen 14 further contains space consuming means 17 that is in layered contact with a contacting surface of carrier means 15. In lumen 14 both carrier means 15 and space consuming means 17 have a shape that corresponds to the internal shape of lumen 14.

Figure 8:
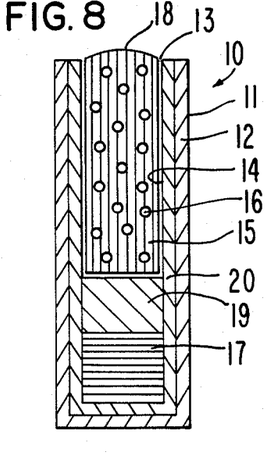

FIG. 8 is an opened view of another embodiment of dispenser 10. In FIG. 8 dispenser 10 comprises an exterior wall 12 that surrounds interior wall 20. In this manufacture exterior wall 12 and interior wall 20 jointly define internal space 14. Internal space 14 contains pharmaceutical carrier means 15 having tiny pills 16 dispersed therein, a density member 19 in contact with carrier means 15 and a space consuming means 17 in contact with density member 19. In this manufacture space consuming means 17 is distant from carrier means 15. In space lumen 14 carrier means 15, density member 19 and space consuming means 17 all embrace a shape that corresponds to the internal shape of space 14.

Figure 9:
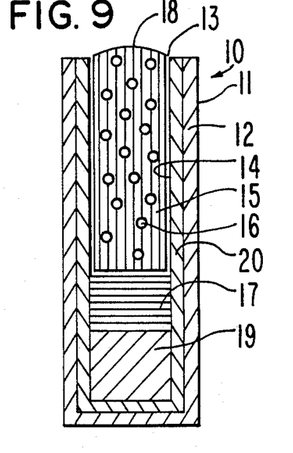

FIG. 9 is an opened view of another manufacture of dispenser 10. In FIG. 9 space consuming means 17 is in contact with the pharmaceutical carrier means 15 and density member 19 is distant from pharmaceutical carrier 15. In a presently preferred embodiment as space consuming means 17 imbibes fluid and takes up space in lumen 14, it forms within itself an immiscible boundary at the interface defined by means 15 and means 17.

Figure 10:
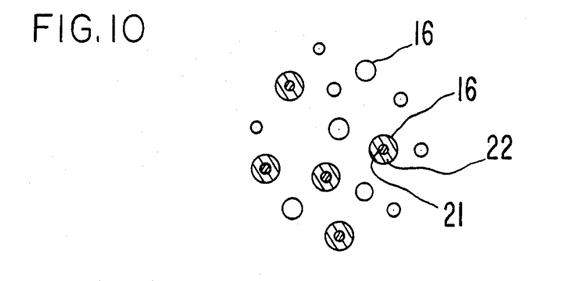

FIG. 10 depicts tiny pills 16 in detail. In FIG. 10 tiny pills 16 comprise a core of beneficial agent 21, such as a drug, surrounded by a wall 22 of a wall forming release rate controlling composition. In one embodiment tiny pills 16 can have wall 22 made from a material that releases beneficial agent 21 in the stomach, or in another embodiment tiny pill 16 can have a wall 22 comprising an enteric composition which prevents release of agent 21 in the stomach, but will release agent 21 in the intestine. Additionally, the materials comprising wall 22 can be selected from materials that release agent 21 by different physical-chemical mechanisms. These mechanisms for tiny pill 16 include erosion, diffusion, osmotic bursting, metabolism, and the like. Wall 22 can have various thicknesses as an additional aid for providing timed release of agent 21.

In the drawing figures and in the specification like parts in related figures are identified by like numbers. The terms appearing earlier in the specification and in the description of the drawing figures, as well as embodiments thereof, are further detailed elsewhere in the disclosure.

DETAILED DESCRIPTION OF THE INVENTION

In accordance with the practice of this invention it has been found that dispenser 10 can be manufactured with a lumen that houses in a cooperative relationship in the lumen carrier means 15, tiny pills 16, space consuming means 17 and, in other optional embodiments, density member 19. The dispenser 10 is formed by wall 12 comprising a composition that does not adversely affect the carrier, the beneficial agent, the tiny pills, the space consuming means, the density member and other ingredients such as an osmagent, an osmopolymer, a gas generating couple, and the like, that can be housed in dispenser 10. Wall 12 is permeable, in at least a part, to the passage of an external fluid such as water and biological fluids and it is substantially impermeable to the passage of beneficial agent, tiny pills, osmagents, osmopolymers, and the like. The wall comprises a material that does not adversely affect an animal, or host, or the components comprising the dispenser and the selectively semipermeable materials used for forming the wall are nonerodible and they are insoluble in fluids.

In one embodiment typical selectively semipermeable materials for forming the wall are cellulose esters, cellulose ethers and cellulose ester-ethers. These cellulosic polymers have a degree of substitution, D. S., on the anhydroglucose unit, from greater than 0 up to 3, inclusive. By degree of substitution is meant the average number of hydroxyl groups originally present on the anhydroglucose unit comprising the cellulose polymer that are replaced by a substituting group. Representative compositions include a member selected from the group consisting of cellulose acylate, cellulose diacylate, cellulose triacylate, cellulose acetate, cellulose diacetate, cellulose triacetate, mono-, di- and tricellulose alkanylates, mono-, di- and tricellulose aroylates, and the like. Exemplary polymers include cellulose acetate having a D.S. up to 1 and an acetyl content up to 21%; cellulose acetate having an acetyl content of 32 to 39.8%; cellulose acetate having a D. S. of 1 to 2 and an acetyl content of 21 to 35%; cellulose acetate having a D.S. of 2 to 3 and an acetyl content of 35 to 44.8%, and the like. More specific cellulosic polymers include cellulose propionate having a D.S. of 1.8 and a propyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentanoate, co-esters of cellulose such as cellulose acetate butyrate and cellulose acetate propionate, and the like.

Additional polymers include ethyl cellulose of various degrees of etherification with ethoxy content of from 40% to 55%, acetaldehyde dimethyl cellulose acetate; cellulose acetate ethyl carbamate; cellulose acetate methyl carbamate; cellulose acetate dimethyl aminoacetate; semipermeable polyamides; semipermeable polyurethanes; semipereamble sulfonated polystyrenes; semipermeable cross-linked selective polymers formed by the coprecipitation of a polyanion and a polycation as disclosed in U.S. Pat. Nos. 3,173,876; 3,276,586; 3,541,0905; 3,541,006 and 3,546,142; semipermeable polymers as disclosed by Loeb and Sourirajan in U.S. Pat. No. 3,133,132; semipermeable lightly cross-linked polystyrene derivatives; semipermeable cross-linked poly(sodium styrene sulfonate); semipermeable cross-linked poly(vinylbenzyltrimethyl ammonium chloride); semipermeable polymers exhibiting a fluid permeability of $2.5 \times 10^{-11}$ to $2.5 \times 10^{-4}$ (cm$^2$/hr·atm) expressed per atmosphere of hydrostatic imbibition, or osmotic pressure difference across the semipermeable wall. The polymers are known to the art in U.S. Pat. Nos. 3,845,770; 3,916,899 and 4,160,020; and in *Handbook of Common Polymers* by Scott, J. R. and Roff, W. J. (1971) published by CRC Press, Cleveland, OH.

Further, in accordance with the practice of this invention, it has now been found that internal wall 20 of dispenser 10 can be made as a capsule member. The capsule member generally is tubular shaped and it has a mouth at one end, and at the end distant therefrom it is closed in a hemispherical or dome shaped end. The capsule member serves as a hollow body having a wall 20 that surrounds and defines an interior compartment 14 provided with an opening 13 for establishing communication with the exterior of the capsule and for filling the capsule.

In one embodiment a capsule is made by dipping a mandrel, such as a stainless steel mandrel, into a batch containing a solution of a capsule wall forming material to coat the mandrel with the material. Then the mandrel is withdrawn, cooled and dried in a current of air. The capsule is stripped from the mandrel and trimmed to yield a capsule with an internal lumen. The materials used for forming the capsule are the commercially available materials including gelatin, gelatin having a viscosity of 15 to 20 millipoises and a bloom strength up to 150 grams; gelatin having a bloom value of 160 to 250; a composition comprising gelatin, glycerine water and titanium dioxide; a composition comprising gelatin, erythrosin, iron oxide and titanium dioxide; a composition comprising gelatin, glycerine, sorbitol, postassium sorbate and titanium dioxide; a composition comprising gelatin, acacia, glycerin and water; water soluble polymers that permit the transport of water therethrough and can be made into capsules, and the like.

Wall 12 also can comprise a flux regulating agent. The flux regulating agent is a compound added to assist in regulating the fluid permeability or flux through the wall 12. The flux regulating agent can be a flux enhancing agent or a flux decreasing agent. The agent can be preselected to increase or decrease the liquid flux. Agents that produce a marked increase in permeability to fluid, such as water, often are essentially hydrophilic, while those that produce a marked decrease to fluids, such as water, are essentially hydrophobic. The amount of regulator in the wall when incorporated therein generally is from about 0.01% to 20% by weight, or more. The flux regulator agents in one embodiment that increase flux include polyhydric alcohols, polyalkylene glycols, polyalkylenediols, polyesters of alkylene glycols, and the like. Typical flux enhancers include polyethylene glycol 300, 400, 600, 1500, 4000, 6000 and the like; low molecular weight glycols such as polypropylene glycol, polybutylene glycol and polyamylene glycol; the polyalkylenediolx such as poly(1,3-propanediol), poly(1,4-butanediol), poly(1,6-hexanediol) and the like; aliphatic diols such as 1,3-butylene glycol; 1,4-pentamethylene glycol; 1,4-hexamethylene glycol, and the like; alkylene triols such as glycerine; 1,2,3,-butanetriol; 1,2,4,-hexanetriol; 1,3,6-hexanetriol, and the like; esters such as ethylene glycol dipropionate; ethylene glycol butyrate; butylene glycol dipropionate; glycerol acetate esters, and the like. Representative fluid decreasing agents include phthalates substituted with an alkyl, an alkoxy or with both an alkyl and alkoxy groups such as diethyl phthalate, dimethoxyethyl phthalate, dimethyl phthalate and [di(2-ethyl-hexyl)alkyl phthalate], aryl phthalates such as triphenyl phthalate and butyl benzyl phthalate; insoluble salts such as calcium sulphate, barium sulphate, calcium phosphate and the like; insoluble oxides such as titanium oxide; polymers in powder, granule and like forms such as polystyrene, polymethylmethacrylate, polycarbonate and polysulfone; esters such as citric acid esters esterfied with long chain alkyl groups; inert and substantially water impermeable fillers; resins compatible with cellulose based wall forming materials and the like.

Other materials that can be used to form the wall 12 for impairing flexibility and elongation properties to the wall, for making wall 12 less-to-nonbrittle and to render tear strength, include phthalate plasticizers such as dibenzyl phthalate, dihexyl phthalate, butyl octyl phthalate, straight chain phthalates of six to eleven carbons, di-isononyl phthalate, di-isodecyl phthalate, and the like. The plasticizers include nonphthalates such as triacetin, dioctyl azelate, epoxidized tallate, tri-isoctyl trimellitate, tri-isononyl tri mellitate, sucrose acetate isobutyrate, epoxidized soybean oil and the like. The amount of plasticizer in a wall when incorporated therein is about 0.01% to 20% by weight, or higher.

Representative of means 17 for manufacturing space consuming means 17 for urging pharmaceutically carrier means 15 from lumen 14 through mouth 13 are at least one of a member selected from the group consisting of an osmopolymer, an osmagent and a gas generating couple. Exemplary of an osmopolymer that can be used for the present purpose is a hydrogel. The hydrogel in the dispenser comprises a shape that corresponds to the internal shape of lumen 14. The hydrogel composition is noncross-linked or, optionally, cross-linked and it possesses osmotic properties such as the ability to imbibe an exterior fluid through semipenmeable wall 12 and exhibits an osmotic pressure gradient across semipermeable wall 12 against a fluid outside dispenser system 10. The materials used for forming the space consuming member that are swellable and expandable are polymeric materials neat and, optionally, polymeric materials blended with osmotic agents that interact with water or biological fluid, absorb the fluid and swell or expand to an equilibrium state. The polymer exhibits the ability to retain a significant fraction of imbibed fluid in the polymer molecular structure. The polymers in a preferred embodiment are gel polymers that can swell or expand to a very high degree, usually exhibiting a 2 to 50 fold volume increase. The swellable, hydrophilic polymers, also known as osmopolymers can be noncross-linked or lightly cross-linked. The cross-links can be covalent or ionic bonds with the polymer possessing the ability to swell in the presence of fluid, and when cross-linked it will not be dissolved in the fluid. The polymer can be of plant, animal or synthetic origin. Polymeric materials useful for the present purpose include poly(hydroxyalkylmethacrylate) having a molecular weight of from 5,000 to 5,000,000; poly(vinylpyrrolidone) having a molecular weight of from 10,000 to 360,000; anionic and cationic hydrogels; poly(electrolyte) complexes; poly(vinylalcohol) having a low acetate residual; a swellable mixture of agar and carboxymethyl cellulose; a swellable composition comprising methyl cellulose mixed with a sparingly cross-linked agar; a polyether having a molecular weight of from 10,000 to 6,000,000; water swellable copolymer produced by a dispersion of finely divided copolymer of maleic anhydride with styrene, ethylene, propylene, or isobutylene; water swellable polymer of N-vinyl lactams; and the like.

Other gelable, fluid imbibing and retaining polymers useful such for forming the hydrophilic, expandable push member 17 include pectin having a molecular weight ranging from 30,000 to 300,000; polysaccharides such as agar, acacia, karaya, tragacanth, algins and guar; Carbopol ®, an acrylic acid polymer, a carboxyvinyl polymer, sometimes referred to as carboxypolymethylene, a polymer of acrylic acid cross-linked with a polyallyl ether of succrose, as described in U.S. Pat. Nos. 2,798,053 and 2,909,462 and available as Carbopols ® 934, 940 and 941, and its salt derivatives; polyacrylamides; water-swellable indene maleic anhydride polymers; Good-rite ® polyacrylic acid having a molecular weight of 80,000 to 200,000; Polyox ® polyethylene oxide polymers having a molecular weight of 100,000 to 5,000,000; starch graft copolymers; Aqua-Keep ® acrylate polymers with water absorbability of about 400 times its original weight; diesters of polyglucan; a mixture of cross-linked polyvinyl alcohol and poly(N-vinyl-2-pyrrolidone); zein available as prolamine; poly(ethylene glycol) having a molecular weight of 4,000 to 100,000, and the like. In a preferred embodiment, the expandable member is formed from polymers and polymeric compositions that are thermoformable. Representative polymers possessing hydrophilic properties are known in U.S. Pat. Nos. 3,865,108; 4,002,173; 4,207,893; 4,327,725, and in *Handbook of Common Polymers*, by Scott and Roff, published by Cleveland Rubber Company, Cleveland, OH.

The osmagent that can be used for the purpose of providing space consuming means 17 comprise inorganic and organic compounds that exhibit an osmotic pressure gradient against an external fluid across semipermeable wall 12. Osmagents are also known as osmotically effective compounds and as osmotically effective solutes. The osmagent imbibes fluid from the outside of dispenser 10 into lumen 14 causing it to produce a solution or a suspension that continuously occupies more space in lumen 14. As more fluid is imbibed into lumen 14, it exerts a pressure against pharmaceutically acceptable carrier 15 pushing it from dispenser 10. Osmotically effective compounds useful for the present purpose include inorganic and organic salts, polysaccharides, carbohydrates, and the like. Representative solutes include magnesium sulfate, magnesium chloride, sodium chloride, potassium chloride, lithium chloride, potassium sulfate, sodium carbonate, sodium sulfate, lithium sulfate, sodium sulfate, potassium acid phosphate, calcium lactate, tartaric acid, lactose, fructose, mannitol, sorbitol, and mixtures thereof. The osmotically active compound is initially present in lumen 14 in excess and it can be in particle, crystal, pellet, powder or granule form. The osmotic pressure of an osmotic compound can be measured with a commercially available osmometer identified as Vapor Pressure Osmometer, Model 2B, available from Hewlett-Packard, Avondale, PA., other osmometers such as the Knauer Vapour Pressure Osmometer can be used for the present purpose. The osmotic pressure in atmospheres, atm, of osmagents suitable for this invention will be greater than zero atm, generally from zero atm up to 500 atm, or higher.

The osmotically effective compound that can be blended homogeneously or heterogeneously with the swellable polymer, to form a push member 17, are the osmotically effective solutes that are soluble in fluid, imbibed into the swellable polymer, and exhibit an osmotic pressure gradient across the semipermeable wall against an exterior fluid. Osmotically effective osmagents useful for the present purpose include magnesium sulfate, magnesium chloride, sodium chloride, lithium chloride, potassium sulfate, sodium sulfate, mannitol, urea, sorbitol, inositol, succrose, glucose, and the like. The osmotic pressure in atmospheres, atm, of the osmagents suitable for the invention will be greater than zero atm, generally from greater than zero atm up to 500 atm, or higher. The swellable, expanable polymer, in addition to providing a driving source 17 for urging carrier 15 containing beneficial tiny pills 16 from dispenser 10, further serves to function as a supporting matrix for an osmotically effective solute. The osmotic solute can be homogeneously or heterogeneously blended with the polymer to yield the desired expandable member 17. The composition in a presently preferred embodiment comprises at least one polymer and at least one osmotic solute. Generally, a composition will comprise about 20% to 90% by weight of polymer and 80% to 10% weight of osmotic solute, with a presently preferred composition comprising 35% to 75% by weight of polymer and 65% to 25% by weight of osmotic solute.

The gas generating couple operable as space occupying means 17 is, in a presently preferred embodiment, an effervescent couple or composition. The gas generating couple comprises at least one preferably solid acidic material and preferably solid basic material that dissolve and react in aqueous fluid that enters the dispenser to produce carbon dioxide. The gaseous generation of carbon dioxide leads to the volume displacement of carrier 15 containing beneficial agent 17 from dispenser 10. The gas generating couple can be present in powder, crystalline, granular, compressed forms, and the like. The acidic or acids that can be used include organic acids such as malic, fumaric, tartaric, itaconic, maleic, citric, adipic, succinic and mesaconic, and the corresponding anhydride such as itaconic anhydride, and citriconic anhydride. Also, inorganic acids such as sulfamic or phosphoric, and the like, can be used for gas generation. Acid salts such as the salts of organic foods can be used including monosodium citrate, potassium acid tartarate, and potassium bitartrate. The basic compounds include metal carbonate and bicarbonate slats such as alkali metal carbonates and bicarbonates, or alkaline earth carbonates and bicarbonates. Exemplary materials include the alkali metals lithium, sodium, potassium carbonate and bicarbonate, and the alkaline earth compounds magnesium and calcium carbonate or bicarbonate. Also useful are ammonium carbonate, ammonium bicarbonate and ammonium sesquecarbonate. The combination of certain of these acids and bases results in a more rapid gas production or effervescence when contacted by water. In particular, either citric acid or a mixture of citric acid and tartaric acid and sodium bicarbonate give a rapid gaseous reaction that can be used for urging carrier 17 from dispenser 10. It will be understood the amount of acidic and basic materials in a couple can vary over a wide range to satisfy the amount of gas generation need to urge carrier 17 form dispenser 10. The essentially anhydrous or dry couple is preferably substantially stoichiometrically balanced to produce a combination that generates carbon dioxide. Also, the acid and base materials can be used in any convenient proportion between 1 to 200 parts and 200 to 1 part on a weight basis to produce the desired results. In addition, the gas generating material can be a substance that generates gas on contact with water such as calcium carbide and carbure.

Pharmaceutically acceptable carrier means 15 in a presently preferred embodiment maintains its physical and chemical integrity inside lumen 14 of dispenser 10. The phrase "maintains its physical and chemical integrity inside lumen 14", used for the purpose of this invention, denotes a carrier formulation that does not substantially undergo change in lumen 14 of dispenser 10. That is, carrier formulation 15 does not hydrolyze, erode, disintegrate or dissolve in lumen 14 during operation of dispenser 10. The expression "nonmeltable", as used for the purpose of this invention means carrier means 15 substantially does not melt inside lumen 14 of dispenser 10. That is, carrier means 15 inside lumen 14 substantially does not change from a solid to a liquid state in lumen 14. Carrier formulation 15, on its delivery from dispenser 10 can, in a fluid biological environment of use such as the gastrointestinal tract of a warm-blooded animal, undergo hydrolysis in the acidic or basic pH of the tract, it can undergo surface erosion, disintegration, dissolution, be hydrolyzed by enzymes, digested by bacteria or fungi, and the like.

Exemplary of carrier formulation means 15 generically includes a member selected from the group consisting of a polyester, polylactide, polyacetal, polyorthoester, polyorthocarbonate, and the like. Representative of more specific carrier formulations 15 includes a member selected form the group consisting of polyglycolic acid exhibiting a Tm of 230° C., wherein Tm is the melting point, polydiglycolide having a Tm of 230° C., polylactic acid having a Tm of 180° C., polydimethylglycoloic acid with a Tm of 240° C., poly carprolactone having a Tm of 63° C., polyalkylene adipate wherein the alkylene group comprises 10 carbons having a Tm of 77° C., polylactideglycolide, and the like.

Representative of additional compositions for forming carrier means 15 comprise polyanhydrides, polyanhydride polymers of sebacic and azelaic acid, hydrophobic polycarbolyic acids having one ionizable carboxylic hydrogen for each 8 to 22 total carbon atoms, bioerodible polymers that innocuously disintegrate or breakdown as a unit structure on release by dispenser 10 such as a hydrophobic polycarboxylic acid having a repeating backbone unit of 8 to 22 carbon atoms for each pendant carboxylic hydrogen; a bioerodible polyvalent ion cross-linked polyelectrolyte with a polyvalent ion selected from the group consisting of aluminum, barium, cadmium, calcium, copper, iron, and zinc with the polyelectrolyte selected for the group consisting carrageenan, pectic acid, pectinic acid and the like; a polyester of the formula [—O—W—CO]y wherein W is an alkylene of 1 to 4 carbons and y is a whole number to provide a polymer having a molecular weight of 4,000 to 100,000; a polyorthoester selected from the group consisting of poly(2,2-dioxo-trans-1,4-cyclohexane dimethylene tetrahydrofuran), poly(2,2-dioxo-1,6-hexamethylene tetrahydrofuran), poly(1,4-cyclohexane dicarbinyl-2,2-dioxotetrahydrofuran), poly (2,2-dioxohexamthylene-1,3-dioxolane), poly(2,2-dioxa-trans-2-methyl-cyclohexane-1,4-diethylene-2-pyrrolidone), poly(2,2-dioxa-cis, trans-1,4-cyclohexane-dimethylene-2-thiocane), and the like. Representative of additional compositions for forming carrier means 15 include polyamino acid, polypepetide, polyglutamate, polyglutamic acid, polylysine, and the like.

Representative of additional polymeric materials for providing carrier means 15 are a hydrophilic polymer selected form the group, consisting of a poly(alginate), poly(carrageenan), poly(guar gum), poly(gum agar), poly(gum arabic), poly(gum ghatti), poly(gum paraya), poly(gum tragacanth), poly(tamarid gum), poly(xanthan gum) and the like. The hydrophilic polymeric material, when used for carrier means 15, comprises a different polymeric composition when a hydrophilic polymeric material is used for space consuming member 17, or when carrier means 17 and space consuming means 17 are in contact with each other.

Carrier means 15, in additional operative embodiments, can be manufactured by (1) compressing water insoluble materials into a shape that corresponds to the internal shape of lumen 14. For example, carrier means 15 can comprise a tableted, an elongated stick-like shape or the like. Carrier means 15, in its additional operative embodiments, maintains its integrity in lumen 14, and on its exit from dispenser 10 disintegrates, or the like, in the fluid environment of use. In this manufacture, carrier means 15 can comprise polymerized particulate composition of matter comprising polyethylene, polyprophylene, cellulose acetate, ethylcellulose, polysulfone, cellulose acetate butyrate, micro-crystalline cellulose, and the like.

Carrier means 15, in another embodiment, can be manufactured from (2) substantially insoluble organic and inorganic substances. Carrier 15, in this embodiment, keeps its shape in lumen 14, but loses its shape in an environment of use. Representative of insoluble organic and insoluble solids used for this purpose comprise a member selected from the group consisting essentially of calcium carbonate, calcium sulfate, diatomaceous earth, clay, silicon dioxide, pulverized glass, and the like.

A carrier means 15, with operative properties can be manufacture in one embodiment, with good properties for engaging in contacting relation wall 12 or wall 20, by compounding a member selected from group (1) with a member selected from group (2). For example, materials selected from (1) and (2) are mixed with each other and with a lubricant or an oil and then with a small quantity of a member selected from the group consisting of a swellable polymer such as gelatin, pectin, and the like, and with an optional disintegrating agent such as solka floc, and the like. The presence of the disintegrating agent in carrier means 15 on carrier means 15's exposure to the environment of use results in the break-up of the carrier into smaller parts with the concurrent release of tiny pills 16 into the environment of use.

Tiny pills 16 comprise a wall composition 22 that surrounds a beneficial agent 21. Wall 22 of tiny pills 16 in one embodiment consists essentially of a fatty ester mixed with a wax. The fatty ester comprises a member such as a triglyceryl ester selected from the group consisting of glyceryl distearate, glyceryl tristearate, glyceryl monostearate, glyceryl dipalmitate, glyceryl tripalmitate, glyceryl monolaurate, glyceryl didocosanoate, glyceryl tridocosanoate, glyceryl monodocosanoate, glyceryl monocaprate, glyceryl dicaparate, glyceryl tricaparate, glyceryl monomyristate, glyceryl dimyristate, glyceryl trimyristate, glyceryl monodecenoate, glyceryl didecenoate and glyceryl tridecenoate.

The wax included in the wall forming composition comprises a member selected from the group consisting essentially of beeswax, cetyl palmitate, spermacetic wax, caranuba wax, cetyl myristate, cetyl palmitate, ceryl cerotate, stearyl palmitate, stearyl mristate, and lauryl laurate.

The composition comprising the ester and the wax can be coated around the drug by using an organic solvent such as a member selected from the group consisting of carbon tetrachloride, chloroform, trichloroethylene, ether, benzene, ethyl acetate, methyl ethyl ketone, isopropyl alcohol, and the like. The fatty esters, waxes, solvents and procedures for making tiny pills that slowly disintegrate and continuously provide drug over a period of 10 to 12 hours are disclosed in U.S. Pat. No. 2,793,979.

Wall 22 of tiny pills 16 in another enbodiment comprises an osmotic wall forming material that releases drug 21 at a controlled rate by the process of osmotic bursting over time. Drug 21 in this embodiment is present in the form of an osmotic solute, such as a therapeutically acceptable salt, and it exhibits an osmotic pressure gradient across wall 22 against an external fluid. The membrane material used to form wall 22 are those permeable to the passage of an external fluid and substantially impermeable to the passage of drug. Typical materials include a member selected form the group consisting of cellulose acylate, cellulose diacylate, cellulose triacylate, cellulose acetate, cellulose diacetate, cellulose triacetate, cellulose acetate having a degree of substitution, D.S., up to 1 and an acetyl content of 21%; cellulose diacetate having a D.S. of 1 to 2 and an acetyl content of 21 to 35%; cellulose triacetate having a D.S. of 2 to 3 and an acetyl content of 35 to 44.8%; cellulose acetyl propionate, cellulose acetate butyrate, and the like. The osmotic wall can be coated around the drug in varying thickness by pan coating, spray-pan coating, Wurster ® fluid air-suspension coating and the like. The wall 22 is formed using organic solvents, including those mentioned above, and solvent systems such as methylene chloride-methanol, methylene chloride-acetone, methanol-acetone, ethylene dichloride-acetone, and the like. Osmotic wall forming material, procedures for forming the wall, and osmotic bursting procedures are disclosed in U.S. Pat. Nos. 2,799,241; 3,952,741; 4,014,334 and 4,016,880.

Wall 22 of tiny pill 16 in another embodiment can comprise a drug release rate controlling material. That is, in one embodiment drug 21 dissolves in the wall and passes through wall 22 at a controlled rate over time. Exemplary materials useful for forming a drug release rate controlling wall include ethylene-vinyl acetate, ethyl cellulose, polyethylene, cross-linked polyvinyl pyrrolidone, vinylidene chlorideacrylonitrile copolymer, polypropylene, silicone, and the like. The wall can be applied by the techniques described above, and materials suitable for forming wall 22 are described in U.S. Pat. Nos. 3,938,515; 3,948,262; and 4,014,335.

Wall 22 of tiny pill 16 in still another embodiment can comprise a bioerodible material that bioerodes at a controlled rate and releases drug 21 to the biological environment of use. Bioerodible materials useful for forming wall 22 include polyvalent acid or alkali mobile cross-linked polyelectrolytes, polycarboxylic acid, polyesters, polyamides, polyimides, polylactic acid, polyglycolic acid, polyorthoesters, and polyorthocarbonates. The polymers and procedures for forming wall 22 are disclosed in U.S. Pat. Nos. 3,811,444; 3,867,519; 3,888,975; 3,971,367; 3,993,057 and 4,138,344.

The expression "active agent 21", as used herein, includes any beneficial agent, or beneficial compound, that can be delivered from the dispenser to produce a beneficial and useful result. The agent can be insoluble to very soluble in the pharmaceutically acceptable carrier 15. The term "active agent", includes algicide, antioxidant, air purifier, biocide, bactericide, catalyst, chemical reactant, fungicide, fermentation agent, fertility inhibitor, fertility promoter, germicide, plant growth promoter, plant growth inhibitor, preservative, rodenticide, sterilization agent, sex sterilant, and the like.

In the specification and the accompanying claims, the term "beneficial agent", also includes drug. The term "drug" includes any physiologically or pharmacologically active substance that produces a local or systemic effect in animals, including warm blooded mammals; humans and primates; avians; household, sport and farm animals; laboratory animals; fishes; reptiles and zoo animals. The term "physiologically" as used herein, denotes the administration of a drug to produce generally normal levels and functions. The term "pharmacologically" denotes generally variations in response to the amount of drug administered to the host. See *Stedman's Medical Dictionary,* 1966, published by Williams and Wilkins, Baltimore, MD.

The active drug that can be delivered includes inorganic and organic compounds without limitation, including drugs that act on the peripheral nerves, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, reproductive system, skeletal system, autacoid systems, alimentary and excretory systems, inhibitory of autocoid systems, alimentary and excretory systems, inhibitory of autocoids and histamine systems. The active drug that can be delivered for acting on these recipients include anticonvulsants, analgesics, antiParkinsons, anti-inflammatories, calcium antagonists, anesthetics, antimicrobials, antimalarials, antiparasites, antihypertensives, antihistamines, antipyretics, alpha-adrenergic agnoist, alpha-blockers, biocides, bactericides, bronchial dilators, beta-adrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, opthalmics, psychic energizers, parasympathomimetics, sedatives, sympathomimetics, tranquilizers, urinary tract drugs, vaginal drugs, vitamins, nonsteroidal anti-inflammatory drugs, angiotensin converting enzymes, polypeptide drugs, and the like.

Exemplary drugs that are very soluble in water and can be delivered by the dispenser of this invention include prochlorperazine edisylate, ferrous sulfate, aminocaproic acid, potassium chloride, mecamylamine hydrochloride, procainamide hydrochloride, amphetamine sulfate, benzphetamine hydrochloride, isoproteronol sulfate, methamphetamine hydrochloride, phenmetrazine hydrochloride, bethanechol chloride, methancholine chloride, pilocarpine hydrochloride, atropine sulfate, scopolamine bromide, isoprpoamide iodide, tridihexethyl chloride, phenformin hydrochloride, methylphenidate hydrochloride, cimetidine hydrochloride, theophylline cholinate, cephalexin hydrochloride, and the like.

Exemplary drugs that are poorly soluble in water and that can be delivered by the dispenser of this invention include diphenidol, meclizine hydrochloride, prochlorperazine maleate, phenoxybenzamine, thiethylperazine maleate, anisindone, diphenadione erythrityl tetrantrate, digoxin, isoflurophate, acetazolamide, methazolamide, bendroflumethiazide, chlorpropamide, tolazimide, chlormadione acetate, phenaglycodol, allupurinol, aluminum aspirin, methotrexate, acetyl sulfisoxazole, erythromycin, progestins, esterogenic, progestational, corticosteroids, hydrocortisone, dydrocortiocosterone acetate, cortisone acetate, triamcinolone, methyltesterone, 17 beta-estradiol, ethinyl estradiol, ethyl estradiol 3-methyl ether, pednisolone, 17 beta-hydroxyprogesterone acetate, 19-nor-progesterone, norgestrel, norethindrone, norethisterone, norethiederone, progesterone, norgesterone, norethynodrel, and the like.

Examples of other drugs that can be delivered by the dispenser include, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chloropromazine, methyldopa, dihydroxyphenylalanine, pivaloyloxyethyl ester of alphamethyldopa hydrochloride, theophylline, calcium glucaonate, ketoprofen, ibuprofen, cephalexin, erythromycin, haloperidol, zomepirac, ferrous lactate, vincamine, diazepam, phenoxybenzamine, diltiazem, milrinone, captopril, madol, quanbenz, hydrochlorothiazide, ranitidine, flurbiprofen, fenbufen, fluprofen, tolmetin, alolofenac, mefenamic, flufenamic, difuninal, nimodipine, nitrendipine, nisoldipine, nicardipine, felodipine, lidoflazine, tiapamil, gallopamil amlodipine, mioflazine, lisinopril, enalapril, captopril, ramipril, endlapriat, famotidine, nizatidine, sucralfate, etintidine, tertatolol, minoxidil, chlordiazepoxide, chlordiazepoxide hydrochloride, diazepam, amitriptylin hydrochloride, impramine hydrochloride, impramine pamoate, and the like. The beneficial drugs are known to the art in *Pharmaceutical Sciences*, 14th Ed., edited by Remington, (1979), published by Mack publishing Co., Easton, PA.; *The Drug, The Nurse, The Patient, Including Current Drug Handbook*, by Falconer, et al., (1974–1976) published by Saunder Company, Philadelphia, PA; *Medicinal Chemistry*, 3rd Ed., Vol. 1 and 2, by Burger, published by Wiley-Interscience, New York; and in *Physicians' Desk Reference*, 38th Ed., (1984) published by Medical Economics Co., Oradell, NJ.

The drug in the tiny pills can be in various forms, such as uncharged molecules, molecular complexes, pharmacologically acceptable salts such as hydrochloride, hydrobromide, sulfate, laurate, palmitate, phosphate, nitrite, borate, acetate, maleate, tartrate, oleate and salicylate. For acidic drugs, salts of metals, amines or organic cations; for example, quarternary ammonium can be used. Derivatives of drugs such as ester, ethers and amides can be used. Also, a drug that is water insoluble can be used in a form that is water soluble derivative thereof to serve as a solute, and on its release from the device, is converted by enzymes, hydrolyzed by pH or other metabolic processes to the original biologically active form. The total amount of beneficial agent number of tiny pills in a dispenser generally is about from 0.05 ng to 10 g or more, with individual dispenser housed in tiny pills containing, for example, 25 ng, 1 mg 5 mg, 10 mg, 25 mg, 125 mg, 250 mg, 500 mg, 750 mg, 1.0 g, 1.2 g, 1.5 g, 4.5 g, 7.5 g, and the like, for administering to a human.

The term "beneficial agent", as used herein, also comprises medicines or drugs, nutrients, vitamins, food supplements and other agents that are administered to farm animals. The dispenser can house various amounts of beneficial agents for administering to a farm animal, which include beneficial agents such as chlortetracycline, ampicillins, penicillins, cephalosporins, and the like; sulfa drugs such as sulfamethazine, sulfathizole, sulfonamiedes, and the like; macrolides such as erythromycin, spiramycin, tylosin, and the like; nitrofurans; antibiotics; ionophores such as lasalocid, salinomycin, virginamycin, and the like; growth-stimulants such as Monesin ® sodium, and Elfazepam ®; defleaing agents such as dexamthazone and fluemthazone; rumen fermentation manipulators; antibloat agents such as organopolysiloxanes; growth promoting agents; minerals, mineral salts and trace elements formulations such as magnesium, copper, cobalt, iron, manganese, molybdenum, zinc, selenium, copper oxide, copper sulfate, cobalt salt, copper salt, selenium salt, selenium disulfied, sodium selenite; inorganic and organic compounds; cobalt oxide, and the like, hormone growth supplements such as stilbestrol; growth efficiency factors, beta-agonist such as denbuterol; vaccines such as bovine diarrhea vaccine; vitamins such as vitamin A, B-group, C, D, E, K, and the like; antienteritis agents such as furazolidone; nutritional supplements such as lysine, lysine monhydrochloride, methionine, mexhionine slats, amino acids, peptides, and the like; beneficial alpha agonists, and the like.

Pharmaceutically acceptable carrier means 15 on leaving lumen 14 of dispenser 10 delivers a beneficial agent 21 in tiny pills 16 to a gastrointestinal tract by rate controlled kinetics. For example, the pharmaceutical carrier means 15 can release tiny pills 16 by rate controlled diffusion, by osmosis, by osmotic bursting, by solution leaching, by solubilization by cross-link cleavage, by solubilization of carrier means 15 by hydrolysis, by solubilization of carrier means 15 by ionization of pendant groups, or by solubilization of carrier means 15 by protonation of pendant groups, by solubilization by backbone cleavage. The usual amount of beneficial agent 21 in tiny pills for farm animals is from 75 ng to 50 g, for example, 75 ng, 1 mg, 5 mg, 100 mg, 250 mg, 500 mg, 750 mg, 1.5 mg, 2 g, 5 g, 10 g, 25 g, and the like. A single dispenser can be administered to a farm animal, for example to a ruminant during a therapeutic program. Dispensers can be provided that have a rate of release from 5 micrograms to 5 grams per day, or higher, for a farm animal.

Representative of beneficial medicaments that can be dispensed to a farm animal using the deliver system 10 of this invention include anthelmintics such as benzimidazole, mebendazole, levamisole, albendazole, cambendazole, fenbendazole, parbendazole, oxfendazole, osybnedazole, thiabendazole, tichlorfon, praziquantel, thiphanate, morantel, morantel tartrate, pyrantel, pyrantel tartrate, methoprene, and the like; antiparasitic agents for the management of endoparasites and ectoparasites, such as avermectin and ivermectin, as disclosed in U.S. Pat. Nos. 4,199,569 and 4,389,397 both assigned to Merck & Co., and in *Science,* Vol. 221, pp 823–828, (1983), where in said ivermectin antiparasitic drugs are disclosed as useful for aiding in controlling commonly occurring infestations in farm animals, such as roundworms, lung worms and the like; and said ivermectin also being used for the management of insect infestations such as grub, lice, mange mite, mite, ticks, larvae, flies such as larve warble fly, dungbreeding fly, larve and flies in the excreta of animals; and the like, with delivery system administering from 5 micrograms per kilogram per day (5 micro/kg/d), to 250 milligrams per day 250 milligrams per day (250 mg/kg/d), to cattle for establishing avermectin, including ivermectin, blood levels; antimicrobial agents such as chloretetracycline, oxytetracycline, tetracycline, streptomycin, dihydrostreptomycin, bacitracins, erythomycin, by biodegradation, bioerosion, enzymatic action, by oxidation, by reduction, by proteolysis, by displacement, by dissolution, by disintegration and the like.

The density member 19, also referred to as densifier 19, used in dispenser 10 is dense enough to retain dispenser 10 in the rumen-reticular sac of a ruminant. Density member 19 lets dispenser 10 remain in the rumen over a prolonged period of time rather than letting it passing into the alimentary tract and be eliminated therefrom. As system 10 remains in the rumen, tiny pills 16 are delivered by system 10 at a controlled rate to the ruminant over time. Generally, dense member 19 will have a density of from about 0.8 to 8 or higher, with the density in a presently preferred embodiment exhibiting a specific gravity of from 1.2 to 7.6. For the ruminants, cattle and sheep, it is presently preferred dense member 19 exhibit a density such that there is a resulting system density of about .3 gm/ml. Materials that have a density that can be used for forming dense member 19 include iron, iron shot, iron shot coated with iron oxide, iron shot magnesium alloy, steel, stainless steel, copper oxide, a mixture of cobalt oxide and iron powder, and the like. Dense member 19 in delivery system 10 can embrace different embodiments. For example, dense member 19 can be machined or cast as a single, solid piece made of stainless steel having a density of 7.6 gm/ml. The solid member is made having a curved shape that corresponds to the internal shape of system 10. The solid member can have an axially aligned bore that extends through the length of the unit member. In another embodiment, dense member 19 can compose a plurality of dense pellets. Density member 19 is described above consists of means having a specific gravity greater than the fluid environment of use for keeping dispenser 10 in the fluid environment over time.

The semipermeable wall forming composition can be applied to the exterior surface of a dispenser alone or in laminar arrangement by molding, air spraying, dipping or brushing with a semipermeable wall forming composition. Other and presently preferred techniques that can be used for applying the semipermeable wall are the air suspension procedure and the pan coating procedures. The air procedure consists in suspending and tumbling the lumen forming components in a current of air and a semipermeable wall forming composition until the wall surrounds and coats the components, The procedure optionally can be repeated with a different semipermeable wall forming composition to form a semipermeable capsule laminated wall. The air suspension procedure is described in U.S. Pat. No. 2,799,241; *J. Am. Pharm. Assoc.,* Vol. 48, pp 451–459, (1979); and *ibid.* Vol. 49, pp 82–84, (1960). Other standard manufacturing procedures are described in *Modern Plastics Encyclopedia,* Vol. 46, pp 62–70 (1969); and in *Pharmaceutical Sciences,* by Remington, 14th Edition, pp 1626–1678, 1970, published by Mack Publishing Co., Easton, PA. In those manufactures wherein the wall is coated by air suspension or by pan coating techniques, mouth 13 is formed in the wall by one of a number of techniques such as laser cutting, milling, sawing, drilling and the like, wherein the device or the mouth-cutting tool is in motion or is stationary.

Exemplary solvents suitable for manufacturing the wall 12 include inert inorganic and organic solvents that do not adversely harm the materials, the capsule wall, the beneficial agent, the carrier composition, the expandable member, the dense member, and the final dispenser. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloriethane, ethyl ether, isopropyl ether, cyclohexane, cyclo-octane, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol.

DESCRIPTION OF EXAMPLES OF THE INVENTION

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

A dispenser comprising tiny pills of a sympathomimetic drug is prepared as follows: first, powdered drug is mixed with sucrose and the blend passed through a 20 mesh screen to produce a multiplicity of cores of drug. Then, a wall-forming composition comprising 85% glycerol monostearate and 15% beeswax in warm carbon tertrachloride is sprayed around the cores in a revolving coating pan until a wall is formed that individually surrounds the cores. Next the solvent is stripped from the tiny pills and the pills dried in a moving air stream.

Next, 190 g of poly(2,2-dioxo-trans-1,4-cyclohexanedimethylene tetrahydrofuran) is heated on a laboratory Teflon ® pan equipped with a surface thermometer to about 150° C., and then the tiny pills are added thereto to provide a homogeneous composition. Then, the composition is molded into a cylindrical shaped and cooled to room temperature. Next, the bioerodible composition is placed into a wide mouth capsule previously charged at its closed bottom first with a 30 g stainless steel density member and then with an expandable driving member. The driving member comprises 2 g of sodium chloride and 5 g of sodium salt of polyacrylic acid available as Carbopol® 934P previously pressed into a tablet. The tablet is formed using an 18.2 mm tableting tool and 3½ tons of compression force. The tablet compresses a final shape that corresponds to the internal shape of the opening of the capsule, the expandable tablet has a surface in contact with the pharmaceutical carrier tiny pill composition. Next, the capsule is coated on its exterior surface up to its mouth by dipping it into wall forming composition. The wall forming composition comprises 1.8 g of 91% cellulose acetate butyrate and 9% polyethylene glycol 400. The wall is applied from a 5% wt/wt solution of methylene chloride methanol 90:10 v/v solvent system. The wall coated dispenser is dried at about 25° to 30° C. for 24 hours. The dispenser provided by this example delivers the tiny pills over time.

EXAMPLE 2

A dispenser is made according to the procedure set forth in Example 1, except that in this example, the beneficial agent is ivermectin, and the pharmaceutically acceptable carrier comprises a condensation copolymer of 3.9-bis(ethylidence)-2,4,8,10-tetraoxospiro[5.5] undecane and 1,6-hexanediol. The copolymer can be prepared according to the synthesis described in U.S. Pat. No. 4,304,767.

EXAMPLE 3

A dispenser is prepared by coating ivermectin in a fluid air suspension machine with a composition of ethyl cellulose in ethanol to surround the beneficial agent ivermectin with a wall of ethyl cellulose for protecting the tiny pills. After the solvent is vacuum stripped form the tiny pills, the pills are blended with the pharmaceutical carrier of Example 1.

EXAMPLE 4

A dispenser system is prepared as follows: first, the body section of a capsule is positioned with its mouth in an upright position, and a dense stainless steel element inserted into the hemispherical end of the capsule. The dense element is machined and its shape made to match the internal shape of the capsule. Next, a layer of an expandable, swellable composition is charged on top of the dense element. The composition comprises 25% by weight of sodium chloride and 75% by weight of poly-(ethylene oxide) having a molecular weight of 200,000. The expandable forming ingredients are blended in a commercial blender with heat for 20 minutes to yield a homogeneous composition. The warm composition is charged into the capsule forming a layer that occupies about ⅓ of the capsule; next, a pharmaceutical carrier comprising tiny pills of cellulose acetate surrounding a core of ivermectin is charged into the open capsule. The cellulose acetate has an acetyl content of 32% and the wall is formed from a methylene chloride methanol solvent. The tiny pills are dispensed in a carrier comprising polylactide having a molecular weight of about 40,000 dissolved in methylene chloride. The blend is charged into the capsule to form a homogeneous mass and vacuum dried at 60° C. Then, a solution of cellulose acetate, 15 wt %, with an acetyl content of 39.8%, is prepared in a methylene chloride methanol solvent system and the outside surface of the capsule coated with a semipermeable wall while maintaining the mouth open. The wall is applied by dipping it into the coating solution for 15 times, first for a 5 second dip, then for two ten second dips, then for a 30 second dip and then for 1 minute per dip with an intervening 5 minute drying period. Following the dipping the deliver dispenser is dried at room temperature, 72° F., about 22° C., for 5 days. The procedure applies about a 2 mm thick semipermeable wall.

EXAMPLE 5

A dispenser is provided comprising a tube-shaped walled dispenser comprising an opened end and a closed end. The wall comprises 50% cellulose acetate butyrate, 45% poly(sulfone) and 5% acetyl tri-isopropyl citrate. The pharmaceutically acceptable carrier means comprises the polyhydroxyacetate ester polyglycolic acid comprising tiny pills of a cellulose acetate wall surrounding the beneficial agent impramine hydrochloride. The space consuming means comprises poly-(ethylene oxide) having a molecular weight of about 3,000,000 and 30% by weight of potassium chloride.

EXAMPLE 6

A dispenser is provided according to Example 5 wherein the dispenser comprises a hydrophilic expandable member comprising a 70:30 ratio of sodium carboxymethylcellulose to sodium chloride, lubricated with 1% magnesium stearate compressed using 10,000 lbs of force in a Carver® laboratory press.

EXAMPLE 7

An oral administrable delivery dispenser is provided by coating a drug core of isosorbide dinitrate with a cellulose acetate wall having an acetyl content of 32%. A methylene chloridemethanol solvent is used as the vehicle for the cellulose acetate in an air suspension coater. After the solvent is evaporated, the pills are housed in a matrix composition made by wet granulation. The composition comprises 92.5% cellulose acetate, polyethylene oxide and hydroxypropylmethylcellulose in equal amounts. Then, the granules are blended in powdered hydroxypropylcellulose and hydroxypropylmethylcellulose. The final stick matrix comprises 85% tiny pills, 10% hydroxypropylcellulose, 3% hydroxypropylmethylcellulose, 1% cellulose acetate and 1% polyethylene oxide. The wall of the dispenser comprises cellulose acetate with an acetyl content of 32%, which wall in one manufacture is deposited on the core by a spray-coating process. In the above examples the drug can be present in the tiny pill in various forms, such as unchanged molecules, molecular complexes, therapeutically acceptable salts such as hydrochlorides, hydrobromides, sulfates, oleates, and the like. For acid drugs, salts of metals, amines, or organic cations, quaternary ammonium salts can be used. Derivatives of drugs such as esters, ethers and amides can be used. Also, a drug that is water insoluble can be used in a form that is the water soluble derivative thereof to serve as a solute, and on its release from the device is converted by enzymes, hydrolyzed by body pH, or other metabolic processes to the original biologically active form.

The amount of drug present in a tiny timed pill per se generally is about 10 ng to 50 mg, and the number of tiny pills in an oral device is about 5 to 1000, preferably 10 to 100. The tiny pills comprising the wall and inner core of drug have a diameter of at least 1 mm to 7.5 mm, and in a presently preferred embodiment they have a diameter of 2 mm to 5 mm. For oral use, the delivery device comprising the matrix and the tiny pills homogeneously or heterogeneously housed therein can have a conventional shape such as round, oval and the like.

An embodiment of the invention pertains to a method for delivering a beneficial drug to an animal at a controlled rate, which method comprises the steps of: (A) admitting into an animal a dispenser comprising: (1) a wall that surrounds a lumen; (2) means in the lumen for containing tiny timed pills, which means keeps its integrity while in the lumen; (3) a plurality of tiny timed pills in the means, which tiny pills comprise a wall surrounding a drug; (4) means in the lumen for occupying space for urging the means containing the tiny timed pills from the lumen; and (5) a mouth in the wall communicating with the means containing the tiny pills; (B) imbibing fluid through the wall into the lumen at a rate determined by the permeability of the wall and the osmotic pressure gradient across the wall to cause the means for occupying space to absorb fluid, expand and push the means containing the tiny pills through the mouth; and thereby (C) delivering the tiny timed pills comprising the beneficial agent to the animal to produce a beneficial effect over time.

It will be appreciated by those versed in the art, the present invention makes available novel and useful delivery devices for dispensing a beneficial drug over a prolonged period of time. Also, it will be understood by those knowledgeable in the dispensing art that many embodiments of this invention can be made without departing from the spirit and scope of the invention, and the invention is not to be construed as limited, as it embraces all equivalents therein.

We claim:

1. A dispenser for administering a beneficial agent formulation to an animal environment of use, the dispenser comprising:
   (a) a wall that surrounds and defines an internal lumen, the wall comprising at least in part a semipermeable composition that is permeable to the passage of fluid and is substantially impermeable to the passage of a beneficial agent;
   (b) a plurality of tiny pills, the pills comprising:
       (1) a core of a beneficial agent; and
       (2) a wall that surrounds the beneficial agent;
   (c) means in the lumen comprising the plurality of tiny pills, which means substantially maintains its physical and chemical integrity and is substantially nonmeltable in the lumen of the dispenser, said means a carrier for delivering the timy pills from the lumen over time;
   (d) means for occupying an increasing amount of space in the lumen for pushing the means comprising the tiny pills from the dispenser; and,
   (e) a mouth in the dispenser comprising a cross-sectional dimension substantially equal to the cross-sectional dimension of the lumen for delivering the tiny pills to the environment of use.

2. A dispenser for administering a plurality of tiny pills to animal environment of use, the dispenser comprising;
   (a) a wall that surrounds and defines an internal lumen, the wall comprising at least in part a semipermeable composition that is permeable to the passage of fluid and is substantially impermeable to the passage of a beneficial agent;
   (b) means in the lumen for administering a plurality of tiny pills to the animal environment of use, said means substantially maintaining its physical and chemical integrity and is substantially nonmeltable while in the lumen of the dispenser;
   (c) a plurality of tiny pills housed in the means for administering the tiny pills, said tiny pills comprising;
       (1) a beneficial agent formulation; and
       (2) a wall that surrounds the beneficial agent formulation;
   (d) means for occupying an increasing amount of space in the lumen for urging the means for administering the tiny pills from the dispenser;
   (e) means in the lumen for maintaining the dispenser in the animal environment of use over time; and
   (f) an opening in the wall of the dispenser comprising a cross-sectional dimension substantially equal to the cross-sectional dimension of the lumen for communicating with the means for administering the tiny pills to the environment of use.

3. A dispenser for administering tiny pills to an animal environment of use, the dispenser comprising:
   (a) a hollow body member comprising an internal lumen and provided with an opening substantially equivalent to the cross-section of the lumen for establishing communication with the lumen;
   (b) means in the lumen for administering tiny pills to the animal environment of use, said means substantially keeping its integrity in the lumen and is substantially nonmeltable in the lumen;
   (c) a plurality of tiny pills housed in the means for administering the tiny pills, said tiny pills comprising:
       (1) a beneficial drug; and
       (2) a wall that surround the drug;
   (d) means for occupying an increasing amount of space in the lumen for pushing the means for administering the tiny pills from the dispenser;
   (e) a wall that surrounds the hollow body member comprising, at least in part, a semipermeable composition that is permeable to the passage of fluid and substantially impermeable to the passage of a beneficial agent; and
   (f) means in the wall for communicating with the lumen, which means comprises a cross-section dimension corresponding to the cross-section of the means in the lumen for administering the tiny pills.

4. A dispenser for administering tiny pills to an animal environment of use, the dispenser comprising:
   (a) a hollow body member comprising an internal lumen and provided with an opening substantial equivalent to the opening of the lumen for establishing communication with the lumen;
   (b) means in the lumen for administering tiny pills to the animal environment of use, said means substantially keeping its integrity in the lumen and is substantially free of thermal degradation in the lumen of the dispenser
   (c) a plurality of tiny pills in the means for administering the tiny pills, the tiny pills comprising:
       (1) a beneficial drug; and
       (2) a wall that surrounds the drug;
   (d) means for occupying an increased volume in the lumen for displacing the means for administering the tiny pills from the dispenser;
   (e) means in the lumen for maintaining the dispenser in the animal environment over time;
   (f) a wall that surrounds the hollow body member comprising, at least in part, a semipermeable composition that is permeable to the passage of fluid and is substantially impermeable to the passage of the beneficial agent; and (g) means in the wall communicating with the lumen for exposing the means for administering the tiny pills to the animal environment.

5. The dispenser for administering the tiny pills to an animal environment of use according to claim 4, wherein the wall of the tiny pill is semipermeable.

6. The dispenser for administering the tiny pills to an animal environment of use according to claim 4, wherein the wall of the tiny pills comprises an enteric composition.

7. The dispenser for administering the tiny pills to an animal environment of use according to claim 4, wherein the wall of the tiny pills is erodible in the environment of use.

8. The dispenser for administering the tiny pills to an animal environment of use according to claim 4, wherein the wall of the tiny pills comprises a microporous composition.

9. The dispenser for administering the tiny pills to an animal environment of use according to claim 4, wherein the wall of the tiny pills comprises a diffusional polymer.

10. The dispenser for administering the tiny pills to an animal environment of use according to claim 4, wherein the wall of the tiny pills comprises a reverse enteric composition.

* * * * *